US00PP33451P2

(12) United States Plant Patent
Whitaker

(10) Patent No.: US PP33,451 P2
(45) Date of Patent: Sep. 7, 2021

(54) STRAWBERRY PLANT NAMED 'FL 16.30-128'

(50) Latin Name: ***Fragaria* X *ananassa Duchesne***
Varietal Denomination: FL 16.30-128

(71) Applicant: Florida Foundation Seed Producers, Inc., Marianna, FL (US)

(72) Inventor: Vance M. Whitaker, Brandon, FL (US)

(73) Assignee: Florida Foundation Seed Producers, Inc., Marianna, FL (US)

( * ) Notice: Subject to any disclaimer, the term of this patent is extended or adjusted under 35 U.S.C. 154(b) by 0 days.

(21) Appl. No.: 16/985,155

(22) Filed: Aug. 4, 2020

(51) Int. Cl.
*A01H 5/08* (2018.01)
*A01H 6/74* (2018.01)

(52) U.S. Cl.
USPC ..... Plt./208
CPC ..... *A01H 6/7409* (2018.05)

(58) Field of Classification Search
USPC ..... Plt./208, 209
CPC ..... A01H 5/093; A01H 5/0893
See application file for complete search history.

(56) References Cited

U.S. PATENT DOCUMENTS

PP25,574 P3 5/2015 Whitaker et al.
PP30,564 P3 6/2019 Whitaker

OTHER PUBLICATIONS http://www.ffsp.net/wp-content/uploads/2020/07/ITN20-03.pdf; Jul. 28, 2020; 8 pages.*
U.S. Appl. No. 16/985,149, filed Aug. 4, 2020, Whitaker.

* cited by examiner

*Primary Examiner* — Kent L Bell
(74) *Attorney, Agent, or Firm* — Dentons US LLP

(57) ABSTRACT

A new and distinct variety of strawberry (*Fragaria* X *ananassa*), which originated from seed produced by a hand-pollinated cross between 'FL 13.27-142' and 'FL 12.90-53'. The new strawberry, named 'FL 16.30-128', can be distinguished at least by its exceptional conical fruit shape; exceptional sweetness and flavor; and high soluble solids content when grown in West Central Florida or other regions that have a climate similar to that of West Central Florida.

1 Drawing Sheet

Latin name of the genus and species of the plant claimed: *Fragaria* X *ananassa* Duchesne.

Variety denomination: 'FL 16.30-128'.

BACKGROUND OF THE INVENTION

The present invention relates to a new and distinct variety of strawberry plant (*Fragaria* X *ananassa* Duchesne) named 'FL 16.30-128'. This new strawberry plant is distinguished at least by its ability to produce fruit that have consistent conical shape, excellent sweetness and flavor, and high soluble solids content when grown in West Central Florida. Asexual propagation of 'FL 16.30-128' was performed at Balm, Fla., which is also where the selection was made and the plants were tested. 'FL 16.30-128' can be contrasted with 'Florida Brilliance' (U.S. Plant Pat. No. 30,564) and 'Florida127' (U.S. Plant Pat. No. 25,574), which are the current, dominant strawberry varieties in Hillsborough County, Fla. 'FL 16.30-128' is a promising candidate for commercial success because it produces firm, evenly colored, and consistently shaped fruit with excellent flavor throughout the entire Florida market window.

SUMMARY OF THE INVENTION

'FL 16.30-128', when grown in a subtropical climate during the fall, winter, or a combination thereof, can be distinguished from all other strawberry plants by at least the following characteristics: high early fruit yield; consistently well-shaped fruit; bright medium-red fruit; and fruit with high sweetness, flavor and soluble solids content.

'FL 16.30-128' originated in a strawberry breeding plot in Balm, Fla. The seed parent was 'FL 13.27-142', an unreleased, unpatented breeding selection with excellent fruit shape, high soluble solids content and good disease resistance. The pollen parent was 'FL 12.90-53', an unreleased, unpatented breeding selection with high early yields, and excellent fruit size. The seeds resulting from the controlled hybridization were germinated in a greenhouse, and the resulting seedlings were planted and allowed to produce daughter plants by asexual propagation (i.e. by runners). Two daughter plants from each seedling were transplanted to raised beds, where they fruited. 'FL 16.30-128' was selection number 128 of the $30^{th}$ cross in the 2016-2017 seedling trial, and thus was given the breeding trial designation of 'FL 16.30-128'. 'FL 16.30-128' exhibited high early yields of consistently shaped fruit with excellent flavor. 'FL 16.30-128' has been asexually propagated annually by runners; and test plantings have established that the vegetative and fruit characteristics of the propagules are identical to those of the initial daughter plants.

'FL 16.30-128' is believed to be phenotypically most similar to its parents. Nonetheless, 'FL 16.30-128' can be distinguished from its seed parent 'FL 13.27-142' at least by its fruit flavor, lighter fruit color, and more compact plant habit. 'FL 16.30-128' can also be distinguished from its pollen parent 'FL 12.90-53' at least by its fruit flavor, more even fruit color and greater disease resistance.

Currently, 'Florida Brilliance' (U.S. Plant Pat. No. 30,564) and 'Florida127' (U.S. Plant Pat. No. 25,574), are the two dominant strawberries varieties in Hillsborough County, Fla. 'FL 16.30-128' has similar fruit size and early yield to 'Florida Brilliance' (Table 1), but with greater sweetness and flavor and higher soluble solids content than 'Florida Brilliance' (Table 2). 'FL 16.30-128' has smaller fruit size than 'Florida127' and similar sweetness and flavor to 'Florida127'. However, the fruit of 'FL 16.30-128' is more consistently conical in shape than 'Florida127' and has higher acidity (Table 3) giving a more balanced, pleasing flavor.

'FL 16.30-128' is less susceptible to *Botrytis* fruit rot (caused by *Botrytis cinerea*) than both commercial standards but is more susceptible to charcoal rot (caused by *Macrophomina phaseolina*) than both commercial standards.

BRIEF DESCRIPTION OF THE DRAWINGS

'FL 16.30-128' is illustrated by the accompanying photograph that shows 5 month-old specimens. The colors shown are as true as can be reasonably captured by conventional photographic procedures. The photograph was captured in February of 2020 in West Central Florida.

FIG. 1. Shows 5-month-old whole plants, including foliage, and fruit at varying stages of ripeness.

DETAILED BOTANICAL DESCRIPTION

The following detailed botanical description sets forth the distinctive characteristics of 'FL 16.30-128'. The present botanical description is of 'FL 16.30-128' when grown under the ecological conditions that prevail during the winter production season in Balm, Fla., i.e., warm days and cool nights. The plant was 5 months of age when the data was collected. Colors are objectively described using the CIELAB color scale (originally published by the International Commission on Illumination (CIE) in 1976) as measured using a Minolta Chroma Meter CR-400 (Minolta, Ramsey, N.J.) colorimeter with a 1 cm aperture, calibrated against a white tile (Y=85.5, x=0.3164, y=0.3237). When the CIELAB color designations differ from the accompanying photographs, the CIELAB color designations are accurate.

PHENOTYPIC DESCRIPTION OF *FRAGARIA* X *ANANASSA* DUCHESNE 'FL 16.30-128'

Classification:
- *Botanical.*—*Fragaria* X *ananassa* Duchesne.
- *Common name.*—Strawberry.

Parentage:
- *Seed parent.*—'FL 13.27-142'.
- *Pollen parent.*—'FL 12.90-53'.

Plant:
- *Average height.*—15 cm to 20 cm.
- *Average width.*—15 cm to 20 cm.
- *Growth habit.*—Compact, upright.
- *Number of crowns per plant.*—4 to 7 depending on seasonal conditions.
- *Vigor.*—Low-Medium.

Leaf:
- *Overall description.*—Pinnately compound with three leaflets.

Petiole:
- *Average length.*—13.2 cm.
- *Average diameter.*—2.8 mm.
- *Pubescence.*—Light.
- *Pubescence density.*—Sparse.
- *Pose of hairs.*—Perpendicular.
- *Texture.*—Smooth.
- *Anthocyanin presence.*—Absent.
- *Color.*—Light green (L*=61.88, a*=−14.84, b*=35.87).

Petiolule:
- *Length.*—Terminal leaflet: 2.6 mm. Lateral leaflets: 3.4 mm.
- *Diameter.*—1.8-2.2 mm.
- *Color.*—Light green (L*=61.8, a*=−14.84, b*=35.87).

Stipule:
- *Length.*—29 mm to 32 mm.
- *Width.*—14-19 mm along the base of the petiole attachment.
- *Anthocyanin presence.*—Exceedingly infrequent.
- *Color.*—Light green (L*=70.23, a*=−7.39, b*=22.49).

Terminal leaflet:
- *Average length.*—64 mm.
- *Average breadth.*—63 mm.
- *Length/width ratio.*—1.02.
- *Shape in cross section.*—Slightly concave.
- *Color, upper surface.*—Medium-light green (L*=34.68, a*=−11.75, b*=15.78).
- *Color, lower surface.*—Light green (L*=50.31, a*=−12.59, b*=20.11).
- *Glossiness.*—Slight gloss.
- *Base shape.*—Cuneate.
- *Apex descriptor.*—Rounded.
- *Pubescence density.*—Sparse.
- *Texture.*—Moderately smooth.
- *Venation pattern.*—Pinnate.

Secondary leaflets:
- *Average length.*—57 mm.
- *Average breadth.*—60 mm.
- *Length/width ratio.*—0.95.
- *Shape in cross section.*—Slightly concave.
- *Color, upper surface.*—Medium-light green (L*=36.97, a*=−12.45, b*=17.98).
- *Color, lower surface.*—Light green (L*=51.38, a*=−12.77, b*=21.34).
- *Glossiness.*—Slight gloss.
- *Base shape.*—Oblique rounded.
- *Apex descriptor.*—Obtuse.
- *Pubescence density.*—Sparse.
- *Texture.*—Moderately smooth.
- *Venation pattern.*—Pinnate.

Leaflet margins: Crenate, with an average of 20 and 20 serrations per terminal and secondary leaflet, respectively.

Stolons:
- *Number of daughter plants.*—10 to 35 depending on environmental conditions.
- *Anthocyanin presence.*—Occasional.
- *Thickness.*—2 mm to 3 mm.
- *Pubescence.*—Light.

Inflorescence:
- *Time of flowering.*—Partial remontancy, commencing two weeks after establishment and continually thereafter in suitable climate.
- *Flower number per plant.*—45 to 60 flowers over a 4 month Florida growing season.

*Flower height.*—0 to 20 cm above soil surface depending on angle of pedicel.

*Position relative to canopy.*—Flowers open at or slightly above canopy height.

*Branching of the inflorescence.*—At or very close to the crown.

Petals:

*Number.*—5 to 6.

*Length.*—12 to 13 mm.

*Width.*—12 to 14 mm.

*Shape.*—Orbicular.

*Apex.*—Rounded.

*Base.*—Rounded.

*Margin.*—Smooth.

*Average diameter of the corolla* (*i.e. the petals collectively*).—30 mm.

*Average number of stamens.*—24.

*Color, upper surface.*—White (L*=78.65, a*=−1.93, b*=6.47).

*Color, lower surface.*—White (L*=79.15, a*=−1.99, b*=5.51).

Calyx:

*Diameter.*—40-50 mm.

*Diameter of calyx relative to corolla.*—30% greater in diameter.

*Diameter of calyx relative to the fruit.*—10% less to 10% greater in diameter.

*Insertion of calyx.*—Level to slightly inserted.

*Color.*—Medium-light green (L*=48.10, a*=−17.04, b*=24.37).

Sepals:

*Number per flower.*—12-14.

*Length.*—18-20 mm.

*Width.*—6-10 mm.

*Apex.*—Subacute to lobed.

*Margin.*—Smooth.

*Color, upper surface.*—Medium green (L*=41.87, a*=−18.66, b*=25.81).

*Color, lower surface.*—Light green (L*=54.32, a*=−15.41, b*=22.93).

Pedicels: Attached to mature primary fruit and 6 cm to 10 cm in length and 1.7 to 2.1 mm in diameter depending on the time of the season. At peak production, the plant will have several crowns, each producing a truss. Each truss will have 5 to 8 pedicels. Inflorescences branch very close to the crown, rendering the peduncle rarely visible.

Fruit:

*Number per truss.*—5 to 8.

*Shape.*—Medium conical to cordate.

*Average fruit weight.*—23 to 27 g (Table 1).

*Weight, primary fruit.*—22 to 37 g.

*Weight, secondary and tertiary fruit.*—14 to 22 g.

*Length, primary fruit.*—45 to 55 mm.

*Width, primary fruit.*—30 to 40 mm.

*Fruit flavor.*—Similar to 'Florida127' which is the current commercial flavor standard, but having higher acidity than 'Florida127'.

*Fruit soluble solids content* (*brix*).—As high as 9.88% in January 2019 (Table 3).

*Fruit firmness.*—Similar to commercial standards (Table 2).

*Fruit cavity.*—Rare.

*Achenes.*—Slightly sunken, 100 to 270 per fruit.

*External fruit color.*—Glossy medium red (a*=38.6).

*Internal fruit color.*—Medium red (a*=22.6).

*Evenness of color.*—Consistently even.

*Flesh and skin firmness at full ripe stage.*—Very firm.

*Rain damage.*—Similar to 'Florida Brilliance'.

Early yield: Similar to 'Florida Brilliance' (Table 1).

Preferred planting period: October 1$^{st}$ to October 15$^{th}$ in West Central Florida.

Nursery performance: 'FL 16.30-128' produces slightly fewer runners than the commercial standards.

Disease resistance:

*Botrytis fruit rot* (*caused by botrytis cinerea*).—Moderately susceptible.

*Powdery mildew* (*caused by podosphaera aphanis*).—Moderately susceptible.

*Anthracnose fruit rot* (*caused by colletotrichum acutatum*).—Moderately susceptible.

*Charcoal rot* (*caused by macrophomina phaseolina*).—Susceptible.

TABLE 1

Performance of three strawberry genotypes during the 2018-19 and 2019-20 seasons in Balm, Florida.

| | Marketable yield (g/plant) | | | |
|---|---|---|---|---|
| Cultivar | November | December | January | February |
| | 2018-19 | | | |
| 'Florida Brilliance' | 21.4 a[y] | 118.9 a | 140.9 a | 558.3 a |
| 'Florida127' | 30.5 a | 28.6 c | 75.8 b | 557.3 a |
| 'FL 16.30-128' | 19.3 a | 74.4 b | 103.3 ab | 390.8 b |
| | 2019-20 | | | |
| 'Florida Brilliance' | 4.3 b | 104.0 a | 180.7 b | 436.3 a |
| 'Florida127' | 8.3 a | 80.2 b | 259.8 a | 446.7 a |
| 'FL 16.30-128' | 4.2 b | 93.6 ab | 176.0 b | 343.1 b |

| | Marketable yield (g/plant) | | |
|---|---|---|---|
| Cultivar | March | Total | Wt/fruit(g)[z] |
| | 2018-19 | | |
| 'Florida Brilliance' | 173.5 a | 1013.0 a | 28.1 b |
| 'Florida127' | 152.1 a | 806.2 b | 30.4 a |
| 'FL 16.30-128' | 114.1 b | 740.0 b | 26.6 b |
| | 2019-20 | | |
| 'Florida Brilliance' | 180.7 a | 905.8 a | 22.4 c |
| 'Florida127' | 141.3 b | 936.2 a | 27.3 a |
| 'FL 16.30-128' | 155.6 ab | 772.4 b | 24.0 b |

[z]Mean fruit weight was determined by dividing total marketable fruit yield per plot by total marketable fruit number per plot.
[y]Mean separation within columns is by Tukey's HSD test, $P \leq 0.05$.

TABLE 2

Trained sensory panel ratings from seven harvests over two seasons.

| Cultivar | Firmness | Sweet-ness | Sour-ness | Strawberry flavor | Green/unripe flavor |
|---|---|---|---|---|---|
| January 2019 ($n^z$ = 8) | | | | | |
| 'Florida Brilliance' | 5.9 a[y] | 4.7 b | 5.1 a | 3.7 b | 2.0 a |
| 'Florida127' | 5.4 ab | 4.3 b | 4.3 a | 4.2 a | 1.8 a |
| 'FL 16.30-128' | 4.6 b | 5.7 a | 4.9 a | 5.1 a | 1.4 a |
| February 2019 (n = 9) | | | | | |
| 'Florida Brilliance' | 5.5 a | 3.4 b | 5.4 a | 3.7 b | 2.1 a |
| 'Florida127' | 4.9 a | 4.9 a | 3.9 b | 4.5 b | 1.7 a |
| 'FL 16.30-128' | 5.8 a | 5.3 a | 4.9 ab | 5.1 a | 1.4 a |
| March 2019 (n = 8) | | | | | |
| 'Florida Brilliance' | 6.8 a | 3.5 a | 5.4 a | 3.0 b | 2.2 a |
| 'Florida127' | 5.6 b | 4.3 a | 5.6 a | 4.0 a | 1.8 ab |
| 'FL 16.30-128' | 5.7 b | 4.5 a | 5.0 a | 4.1 a | 1.2 b |
| December 2019 (n = 9) | | | | | |
| 'Florida Brilliance' | 6.7 a | 3.9 b | 5.3 a | 3.8 b | 2.5 a |
| 'Florida127' | 5.4 b | 4.9 a | 4.8 a | 5.5 a | 1.6 b |
| 'FL 16.30-128' | 3.9 c | 5.7 a | 5.7 a | 5.8 a | 1.6 b |
| January 2020 (n = 9) | | | | | |
| 'Florida Brilliance' | 4.5 a | 5.5 a | 3.3 a | 4.7 a | 1.0 a |
| 'Florida127' | 4.1 a | 5.8 a | 3.8 a | 4.8 a | 1.4 a |
| FL 16.30-128 | 4.2 a | 5.9 a | 3.9 a | 5.1 a | 0.8 a |
| February 2020 (n = 10) | | | | | |
| 'Florida Brilliance' | 4.5 a | 4.1 a | 5.0 a | 3.8 a | 1.3a |
| 'Florida127' | 4.3 a | 4.7 a | 4.7 a | 4.2 a | 1.1 a |
| 'FL 16.30-128' | 4.6 a | 5.0 a | 5.4 a | 4.2 a | 1.0 a |
| March 2020 (n = 9) | | | | | |
| 'Florida Brilliance' | 6.3 a | 4.7 a | 4.6 a | 4.0 a | 1.1 a |
| 'Florida127' | 4.6 b | 4.8 a | 3.9 a | 4.3 a | 1.2 a |
| 'FL 16.30-128' | 5.4 ab | 5.8 a | 5.2i a | 5.1 a | 0.7 a |

[z]Number of trained panelists

[y]Mean separations within harvest dates and columns are by Tukey's HSD test, P ≤ 0.05

TABLE 3

Soluble solids content (SSC), pH, titratable acidity (TA) and SSC/TA from seven harvests dates over two seasons.

| Cultivar | SSC (%) | pH | TA (%) | SSC/TA |
|---|---|---|---|---|
| January 2019 | | | | |
| 'Florida Brilliance' | 8.09 b[z] | 3.74 a | 0.77 a | 10.5 a |
| 'Florida127' | 8.70 ab | 3.77 a | 0.75 a | 11.7 a |
| 'FL 16.30-128' | 9.88 a | 3.67 a | 0.84 a | 11.8 a |
| February 2019 | | | | |
| 'Florida Brilliance' | 6.09b | 3.77 ab | 0.59b | 10.4b |
| 'Florida127' | 7.39 ab | 3.87 a | 0.55 b | 13.5 a |
| 'FL 16.30-128' | 7.71 a | 3.68 b | 0.73 a | 10.6 b |
| March 2019 | | | | |
| 'Florida Brilliance' | 5.62 b | 3.73 a | 0.61 b | 9.2 b |
| 'Florida127' | 7.46 a | 3.81 a | 0.66 b | 11.3 a |
| 'FL 16.30-128' | 7.40 a | 3.69 a | 0.72 a | 10.2 ab |
| December 2019 | | | | |
| 'Florida Brilliance' | 6.41 b | 3.67 a | 0.81 ab | 7.96 a |
| 'Florida127' | 8.68 a | 3.82 a | 0.72b | 12.13 a |
| 'FL 16.30-128' | 8.38 a | 3.69 a | 0.87 a | 9.67 a |
| January 2020 | | | | |
| 'Florida Brilliance' | 8.43 a | 3.67 a | 0.82 a | 10.56 a |
| 'Florida127' | 9.09 a | 3.63 a | 0.86 a | 10.54 a |
| 'FL 16.30-128' | 9.78 a | 3.73 a | 0.73 a | 13.39 a |
| February 2020 | | | | |
| 'Florida Brilliance' | 6.14 b | 3.76 a | 0.56 b | 10.87 a |
| 'Florida127' | 7.62 a | 3.75 a | 0.61 ab | 12.56 a |
| 'FL 16.30-128' | 7.84 a | 3.68 a | 0.70 a | 11.33 a |
| March 2020 | | | | |
| 'Florida Brilliance' | 8.28 a | 3.63 a | 0.82 a | 10.09 b |
| 'Florida127' | 9.63 a | 3.73 a | 0.78 a | 12.34 a |
| 'FL 16.30-128' | 9.27 a | 3.64 a | 0.86 a | 10.82 ab |

[z]Mean separations within harvest dates and columns are by Tukey's HSD test, P ≤ 0.05

What is claimed is:

1. A new and distinct strawberry plant named 'FL 16.30-128' as illustrated and described herein.

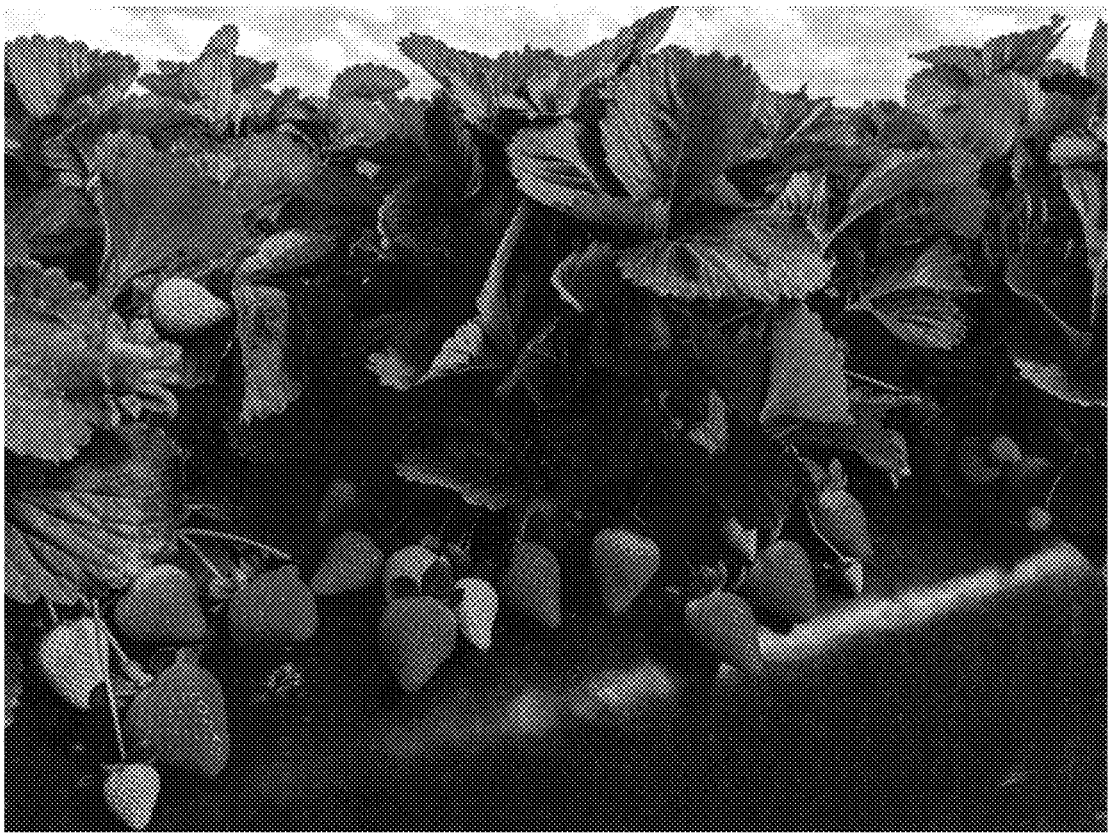

* * * * *